United States Patent

Hörnell et al.

[11] Patent Number: 5,825,441
[45] Date of Patent: Oct. 20, 1998

[54] LIQUID CRYSTAL WELDING GLASS SHIELDS HAVING IMPROVED OPTICAL ANGULAR PROPERTIES

[76] Inventors: Ake Hörnell, Präståkersvägen 29, S-780 40 Mockjärd; Stephen Palmer, Honefsgatan 3-2, S-784 74 Borlänge, both of Sweden

[21] Appl. No.: 569,095
[22] PCT Filed: Apr. 25, 1995
[86] PCT No.: PCT/SE95/00455
§ 371 Date: Dec. 22, 1995
§ 102(e) Date: Dec. 22, 1995
[87] PCT Pub. No.: WO95/29428
PCT Pub. Date: Nov. 2, 1995

[30] Foreign Application Priority Data

Apr. 26, 1994 [SE] Sweden ................................. 9401423

[51] Int. Cl.⁶ ...................................................... G02F 1/36
[52] U.S. Cl. .................. 349/77; 349/73; 349/75; 349/96; 349/81
[58] Field of Search ................. 349/73, 74, 76, 349/77, 81

[56] References Cited

FOREIGN PATENT DOCUMENTS 0 005 417  11/1979  European Pat. Off. .
41 06 019  10/1991  Germany .

Primary Examiner—William L. Sikes
Assistant Examiner—Julie Ngo
Attorney, Agent, or Firm—Young & Thompson

[57] ABSTRACT

A liquid crystal welding glass structure whose density increases when welding is commenced includes two liquid crystal cells which are mounted between polarization filters which have an extinguishing effect on one another. When mounting the filters, the filters are turned so that their respective angular dependencies on the optical density counteract one another. With the intention of improving this compensating effect, the brushing/rubbing of the mutually opposing limiting walls which determine the direction of the molecules is limited to at least one of the component cells whose relative angular displacement differs from 90° and is smaller than or coincident with 85°. The angle is preferably between 20° and 85°.

11 Claims, 3 Drawing Sheets

IF   LC81   4μ90°   LC81   4μ90°   LC81
      90°    TN     0°     TN     90°

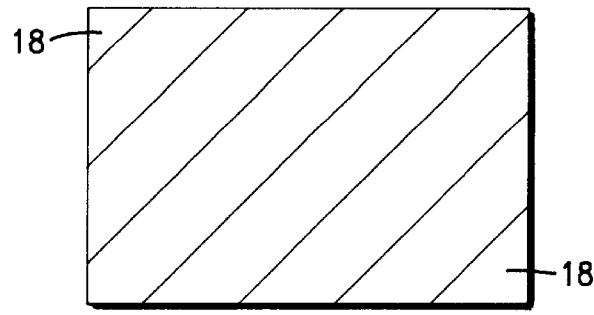
FIG. 3
PRIOR ART
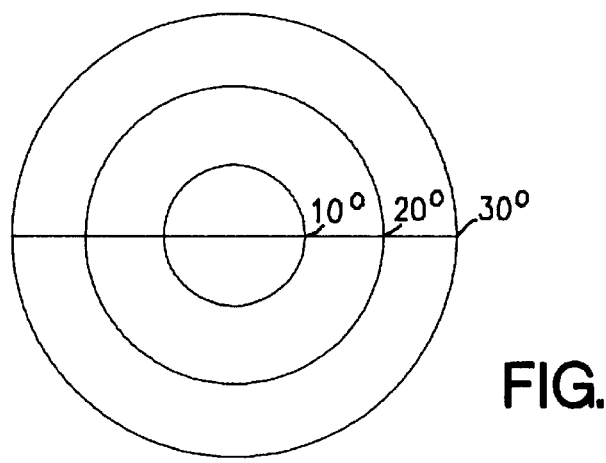
FIG. 4
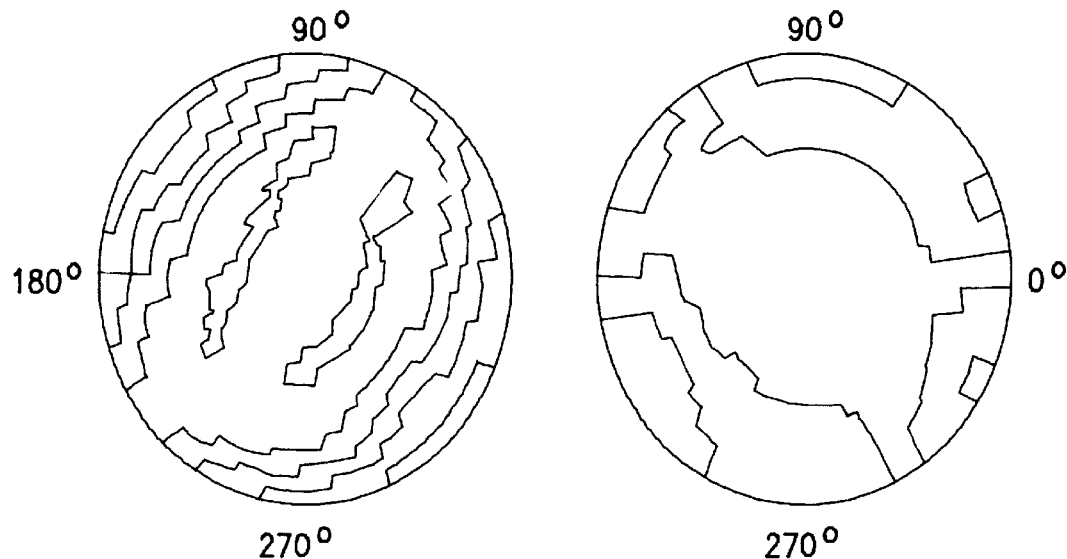
FIG. 5
PRIOR ART
FIG. 6

LIQUID CRYSTAL WELDING GLASS SHIELDS HAVING IMPROVED OPTICAL ANGULAR PROPERTIES

BACKGROUND OF THE INVENTION

1. Field of the Invention

The present invention relates to liquid crystal welding glass shields having improved optical angular properties, and then more specifically to filter constructions according to claim 1.

2. Description of the Related Art

Liquid crystal protective glass shields have been known to the art for many years. These shields are comprised of a combination of crossed polarization filters and layers of liquid crystals and the protective glass is able to change from an opaque state to an elevated transparent state in response to a change in an electric influence, this influence being controlled by the light that falls on a detector when welding is in progress and/or by electromagnetic detection. This enables a welder to perform a welding operation and also to perform tasks outside the welding area without removing the protective shield, because the shield will be clear or transparent when not subjected to the glare of a welding arc and will darken immediately when exposed to such glare.

The filters are normally mounted in a face mask. One particular problem is that the visible area is darkened unevenly due to the fact that the density-filter effect is dependent on the angle of incidence of the ambient light.

An improvement in this respect is taught by U.S. Pat. No. 4,398,803, whereby the liquid crystals are made relatively thin with the product of layer thickness and optical anisotropy (i.e. the difference in refractive index $\Delta n$ between the refractive index of ordinary and extraordinary light rays) reaching to between 150 and 600 nanometers.

In this context, a typical cell construction consists of a twisted nematic (TN) type liquid crystal cell inserted between two mutually crossed polarization filters, where the defining walls are treated with a plastic layer which has been brushed/rubbed in specific directions (the so-called alignment directions), so that the structure in the liquid crystal defining surfaces will force the nematic molecules to each take specific angular positions and so that the molecules will be twisted mutually through 90° between said defining surfaces. Other surface treatment methods which have corresponding effects are also known to the art. In an electrically non-activated state, the polarization plane will be rotated through 90° as light passes through the filter, so as to compensate for the effect of the crossed polaroids and the cell becomes transparent. This rotation of the nematic molecules can be stopped to a greater or lesser extent, by applying an electric field and therewith obtain a filter effect that can also be controlled. However, a cell of this kind has a relatively strong asymmetry in its dark, electrically activated state, with varying absorption of light that is incident at angles other than a right angle, this asymmetry being further amplified by the fact that the nematic molecules nearest the surface, bound by the surface effect, still give rise to a residual optical activity. Thus, when the angles of incident light increase in relation to the normal (i.e. the perpendicular), the filter in the two bisectrix directions between the alignment directions will be more transparent and relatively constant in relation to the directions of the crossed polaroid filters along the direction of one bisectrix while darkening along the direction of the other bisectrix.

OBJECTS AND SUMMARY OF THE INVENTION

It is known to compensate for the asymmetric effect by combining two TN cells which twist through 90°, such that the "weak" bisectrix of one TN cell will coincide with the bisectrix of the other "strong" bisectrix, and vice versa. However, despite this compensation, the field of vision is still uneven, which is troublesome to the user. An object of the present invention is to provide an improvement in this respect.

One particular object of the invention is to provide an improvement with regard to low absorption in the transparent state of the glass. Another object is to provide a protective welding glass which will have variable darkness in its darkened state, so as to enable one and the same protective glass to be used with very strong welding light and with much weaker welding light, so that all types of welding work can be carried out with one and the same protective glass shield to the best possible extent. It is known to the art that the optical activity can be varied by applying different voltages, although the unevenness in the angle-dependent density of the light tends to become more troublesome in the earlier know techniques voltage across the cells is increased.

The most important objects are achieved in accordance with the invention with a liquid crystal welding-glass filter construction of the kind defined in the introduction which has features set forth in the characterizing claim 1.

Thus, in accordance with one aspect of the invention, the concept moves away from the typical twist angle of 90° in "twisted nematics" and, instead, employs a smaller angle which is smaller than 85°, and which preferably lies between 20° and 85°. The improvement is less noticeable between angles of 90° and 80°, but becomes more noticeable from 80° to 70°, and is still more apparent at an angle of 60°, and is the same at 50°. A twist angle of 60°–70° is preferred with liquid crystals that have a thickness of 4 $\mu$m and are comprised of the crystal substance Merck ZLI 3700100. Although the asymmetry becomes more powerful with each individual cell, an improved field homogeneity is nevertheless obtained when two such crystals are combined.

In present-day liquid crystal welding glass there is often used a pigment cell (guest-host-cell) in addition to the TN cells in order to achieve sufficient absorption and to ensure a safety state in the event of a voltage loss. Although such cells have good angular properties in themselves, they nevertheless constitute a complication and may cause the filter to react more slowly than is necessary; A particular aim of the present invention is therefore to be able to eliminate pigment cells by enabling sufficient light to be absorbed by the rotating or twisting cells.

In order to be able to apply the same voltage to two different liquid crystal cells, and therewith simplify the electronics required, it is preferred at present to use two mutually identical cells. However, more degrees of freedom can be gained by relinquishing this condition, and the use of a 90° twist cell in one of the crossed polaroids will furthermore result in low absorption of light at transparent states in the absence of voltage, and a greater degree of darkness upon activation.

One of the problems encountered when using cells having a smaller twist angle than 90°, referred to conveniently as "low-twist cells", resides in achieving high light transmission in the transparent state while, at the same time, obtaining a sufficiently low light transmission in the dark state. Consequently, in accordance with one aspect of the present invention, a "symmetric" polarization filter placement is preferred. When the polarization filters are disposed at mutually intersecting angles of 90°, it is suitable to mount a low-twist cell such that the bisectrix between the surface treatment directions will coincide essentially with a bisectrix between the polarization directions of the filters. The greatest transmission of light will then be obtained in the electrically non-activated state of the device, i.e. its or transparent state.

In accordance with one preferred embodiment of the invention, it is convenient also to reduce the thickness of the liquid crystal cells to an extent greater than that recommended in the aforesaid U.S. patent specification. This results particularly in a reduced switching time, because the switching time is inversely proportional to the square of cell thickness. Thus, the switching time can be reduced in the order of magnitude of 50%, by reducing the thickness of the liquid crystal cells from 4 μm to 3 μm under otherwise equal conditions. This reduction in cell thickness can be achieved by using low-twist cells, by virtue of a dependency that has been found to exist between the value thickness multiplied by optical anisotropy, the twist angle and the light transmission in the light or transparent state. This dependency can be utilized to construct a protective welding glass which has good optical angular properties, high light transmission in the transparent state, and rapid state-switching properties. This is only possible by using low-twist cells with the polarization filters placed in the aforedescribed symmetric manner.

The fundamental cause of this thickness problem is that a cell which does not have appreciable thickness will not function to cleanly rotate optically incident polarized light, and elliptically polarized light will be emitted instead. When this cell is placed between two mutually crossing polarization filters, transmission will vary periodically with the thickness of the cell. The problem is slightly eased when using cells which have a smaller twist angle than 90°. However, an optimal thickness is determined by the twist angle, as illustrated in FIG. 7 and as explained further on. Consequently, in accordance with a preferred embodiment, combinations of the product of thickness and optical anisotropy (a material constant) and twist angle are determined by this curve.

In accordance with another preferred embodiment, a low-twist cell can be placed anti-symmetrically, meaning that the direction of the bisectrix of the acute angle is placed between the treatment directions of the cell (rubbing directions) so as to coincide with the direction of polarization of one polarizer. In a non-activated state, such a construction will exhibit relatively low light transmission, but a more transparent state is obtained when a moderate voltage is applied, this more transparent state returning to a generally darker state when the voltage is again increased. One advantage with this construction is that a loss in voltage will not result in a loss of light absorption and that a given protective effect will remain. This enables the existing standard for protective welding glass which requires the difference between an adjusted state and a state which occurs upon the loss of current supply to be at most nine darkness degrees to be maintained more easily, even at high degrees of darkness. This enables two asymmetric low-twist cells to be used or one symmetric cell and one asymmetric low-twist cell.

BRIEF DESCRIPTION OF THE DRAWINGS

The invention will now be described in more detail with reference to exemplifying embodiments thereof and also with reference to the accompanying drawings.

FIG. 3 illustrates schematically a gray scale which shows how the uneven absorption obtained with the earlier known technique is perceived by user.

FIGS. 4–6 are polar diagrams which illustrate the absorption of light at different angles of incidence. FIG. 4 illustrates the scale used.

FIG. 5 is a polar diagram illustrative of a known type of protective welding glass. FIG. 6 is a corresponding diagram illustrative of an inventive protective welding glass.

DESCRIPTION OF THE PREFERRED EMBODIMENTS

Figure 1:
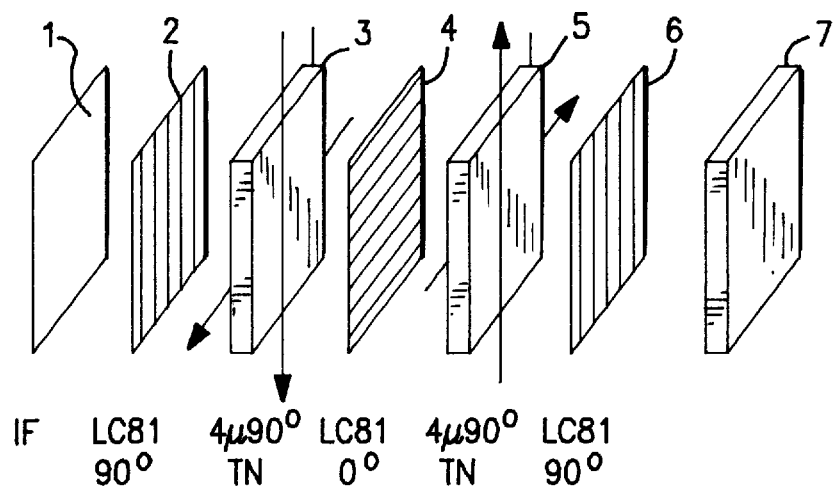
FIG. 1 is an exploded view of a protective welding glass construction according to one known technique (twisted nematic 90°).

The principle exploded view of FIG. 1 shows the various components of a protective welding glass. The outermost component is an interference filter 1 which also functions to eliminate UV light and IR light and limits the wavelength range. There then follows a first polarization filter 2 (polaroid), a first optically rotating liquid crystal cell 3, a second polarization filter 4 whose polarization direction is at right angles to the polarization direction of the first polarization filter 2, a second optically rotating liquid crystal cell 5, and a third polarization filter 6 which has the same direction of polarization as the first polarization filter 2. The arrangement may optionally also include a so-called guest-host-cell 7. This latter cell is not an optically rotating cell but instead includes a nematic liquid crystal, whose molecules and atoms are normally aligned parallel with the polarization direction of the third polarization filter with the aid of prepared glass surfaces. An inmixed pigment having ordered anisotropic absorption is highly absorbent in the aligned state. When a voltage is applied, the molecules of the nematic crystal will position themselves at right angles to said surfaces and therewith cause the molecules of the pigment to move to positions in which the least amount of light is absorbed. Cells of this kind are known to the art. One advantage afforded by such cells over other cells is that they will provide a filter effect in the absence of an applied voltage, whereas remaining cells are light-transparent in the absence of an applied voltage. When a welding filter is taken into use and its control circuits are activated, the filter becomes more open to light. A sensor (not shown) can now detect whether or not welding light enters the filter, wherewith the control circuit (not shown) causes a control voltage to be applied to the cells 3 and 5 while eliminating the voltage to the cell 7. An arrangement of this kind is common to both the invention and to the earlier known technique, insofar that the invention is concerned with the nature of the liquid crystals.

The inwardly facing glass plates of the cells are provided with transparent electrically conductive electrode layers (e.g. stannic oxide layers) on which there is applied, for instance, a polyimide layer which has been treated mechanically, normally by brushing/rubbing in specific directions, according to known techniques in directions that are perpendicular in mutually facing surfaces. According to this known technique, the cells 3 and 5 are turned asymmetrically in relation to one another, for instance so that the first cell surface that receives light in the cell 3 is treated at right angles to the polarization direction of the polaroid filter 2, whereas the first surface that receives light in the cells 5 is treated parallel with the polarization direction of the polarization filter 2. The compensation described in the introduction is achieved herewith.

A welding glass filter arrangement of this kind can be caused to change from its transparent state having a density of 3.6 to density values ranging from 9 to 13, by varying the applied voltage from about 3.3 V to about 4.4 V. The same voltage is applied to both cells.

The density varies because the voltage that strives to orientate the nematic molecules parallel with the electric field is counteracted by the plastic layers on the inner surfaces of the glass, which cause the molecules to be aligned in parallel with the surfaces, and consequently the electrically influenced orientation has its greatest effect therebetween and decreases towards said surfaces. However, in practice, a certain optical activity will always remain due to the surface effects. Consequently, it can be expected that two mutually crossing polaroids will correspond to a density of 10–11 in the absence of a cell, and that the density will vary, in practice, between 4.5 and 6.5 when a cell is included and with respective voltages applied in accordance with the aforegoing.

The density is defined conventionally as $$D=1+7/3\times{}^{10}\log(1/T),$$

where T is the transmission coefficient.

Despite the compensation that is achieved with regard to oblique angles of incidence, the not insignificant differences in the field of vision still remain when practicing this known technique.

Figure 2:
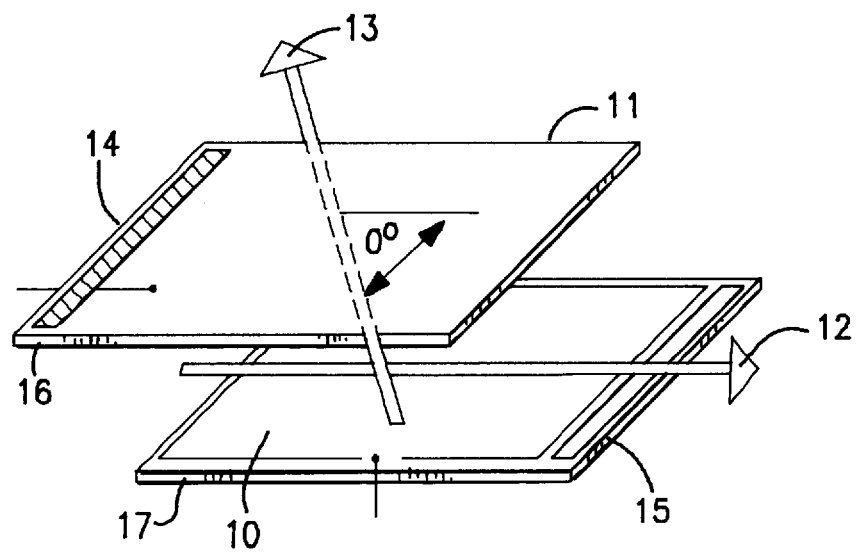
FIG. 2 illustrates two crystal-cell delimiting plates, in accordance with the invention.

Hitherto, the concept of liquid crystal protective welding glass structures has been based on the expected natural geometry that is obtained when orientation of the crystal is twisted through 90° in response to forced conditions at the boundary surfaces. In accordance with the present invention, it has now been found that an improvement can be achieved by reducing the angle through which the crystal is twisted. This is illustrated in FIG. 2, which shows a pair of plates of a liquid crystal cell. The mutually facing surfaces of the plates 10 and 11 are each provided with electrically conductive layers and thin plastic coatings. These layers and coatings are brushed, or rubbed, in accordance with the white arrows 12 and 13 but at a mutual angle θ. According to the earlier known technique, this angle is 90° but is smaller than 90° according to the present invention. As illustrated, the plate arrangement is intended for a cell which rotates naturally in an counter-clockwise direction, although cells which rotate in a clockwise direction are also known. The plates are provided at 14 and 15 with means by which a voltage can be applied. The reference numerals 16 and 17 identify identification marks made on the plate edges.

FIG. 3 illustrates a filter in the protective welding glass included in a welding helmet and shows the filter as seen by the wearer of the helmet. The filter is activated and has a density factor or coefficient in the forward direction, this coefficient, however, being reduced in two directions such that the field of vision at the regions 18 has reduced absorption. This is the subjective image received by the wearer, although in reality the unevenness is not localized in the field but manifests itself in angle-dependent deflections. This angle-dependency has been shown in FIGS. 4–6, where FIG. 4 illustrates the polar coordinate system used in FIGS. 5 and 6, wherein the shaded rings indicate unitary incremental increases in light absorption, from a light or transparent effect to a darker effect in accordance with the aforegiven definition. FIG. 5 therewith illustrates the measuring result obtained with a device having two 90°-twist cells in accordance with known technique, while FIG. 6 illustrates the result obtained when including two 60°-twist cells between pairs of polarization filters. The density is 12 in the case of a 0° rotation in both cases, thus in the forward direction.

Because the angle θ differs from 90°, the filter effect obtained will be far more uniform over varying angles of view. The same crystal material has been used in both cases, and in both cases there have been applied voltages which result in an intended density in accordance with the aforesaid definition of arrow 13, thus resulting in a relatively high damping effect suitable for welding in conditions where very strong welding light is generated. The construction in both cases is the same as that illustrated in FIG. 1, the only difference being that the cells 3 and 5 of the FIG. 5 illustration are twisted through 90°, whereas the cells of the FIG. 6 illustration are twisted through the smaller angle of 60°. Both Figures are polar diagrams with the outermost circle representing a deviation of 30° from a perpendicular angle of incidence. The diagrams have been produced in a stepping machine with the inclination taken in steps of 2° and with an azimuth step of 10°. Curves which represent equal absorptions have been produced in single unit steps.

The examples hitherto mentioned have involved the use of two identical liquid crystal cells. The advantage with this is that both cells can be driven with one and the same voltage, which voltage can be varied to produce different densities. This simplifies the electronics that are required. However, this forced condition no longer applies when more expensive electronics are used, such electronics providing more degrees of freedom for obtaining said compensation.

It then becomes attractive to arrange a first known 90° twist cell between mutually crossing polaroids and to arrange another cell having a twist of 20°–85° between other mutually crossing polaroids, therewith optimizing compensation for absorption errors in the first cell. This increase in the number of degrees of freedom also enables the structure in the polar diagram for the dark state to be influenced.

Different cells may also be combined so as to achieve an optimized total solution, where this optimization is adapted to the desired end result. For instance, it is possible to combine symmetrically and asymmetrically mounted crystals, cells of different twist angles and thicknesses, etc.

Figure 7:
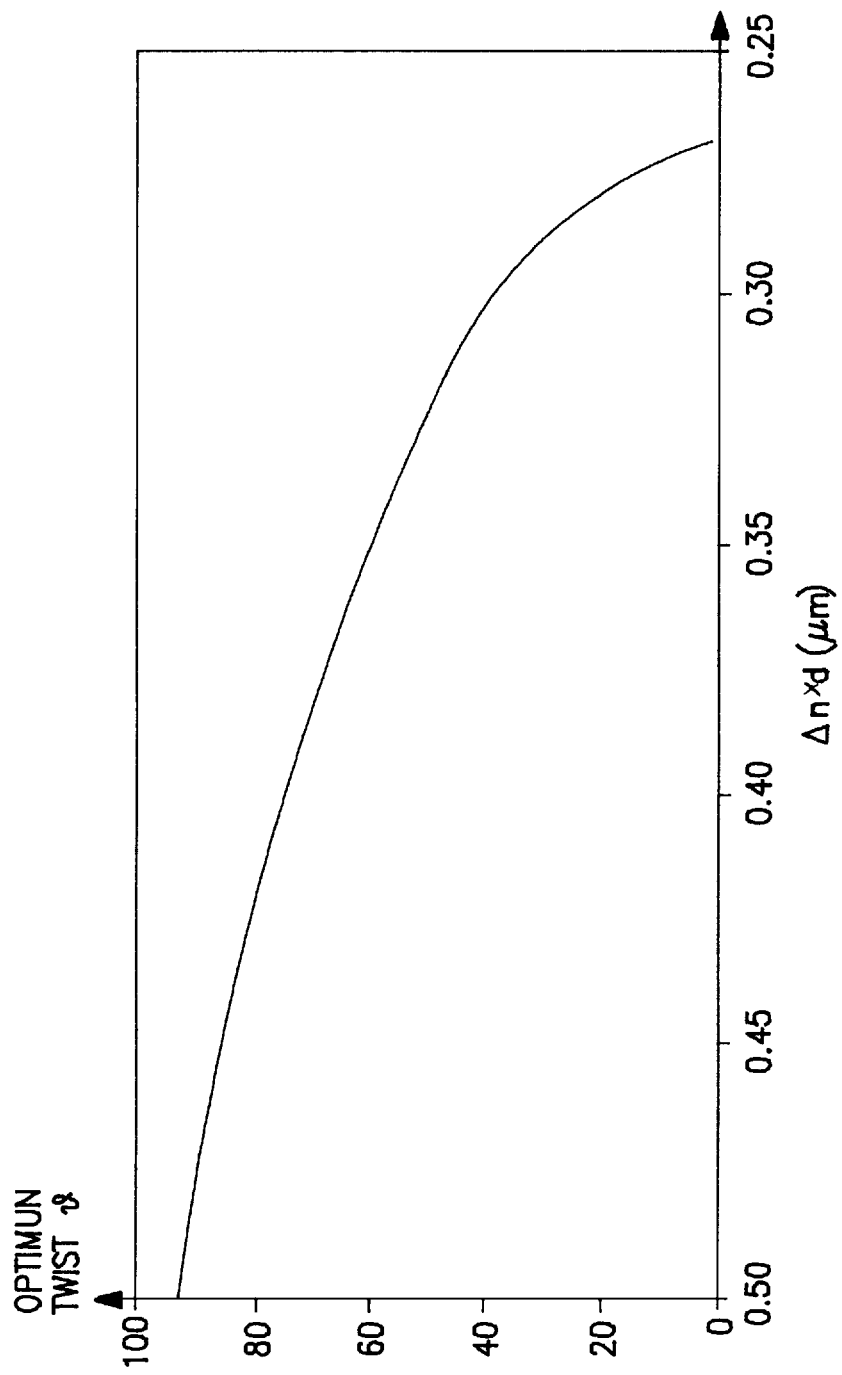
FIG. 7 illustrates how the optimal twist angle varies with the product between the optical anisotropy and the cell thickness.

As earlier mentioned, in relation to earlier known techniques there is good reason not only to reduce the twist angle but also to reduce the thickness of the cell to a corresponding extent. It is proposed in the aforesaid U.S. Pat. No. 4,398, 803 that the thickness of the known 90° twist crystals shall be limited so that the product of the optical anisotropy and the layer thickness, expressed in micrometers, shall reach between 150 and 600 nanometers. According to one aspect of the present invention, it is found that there exists an optimal thickness (or more correctly an optimal product between optical anisotropy and thickness) for each twist angle. The best possible transparent state is obtained at this optimal thickness. The function is shown in FIG. 7.

What is claimed is:

1. A welding glass filter construction that is able to switch rapidly between a high light-absorbing state and a low light-absorbing state, and vice versa, in response to variations in the intensity of welding light comprising two nematic-type liquid-crystal cells disposed between transparent, electrode-loaded plates which can be connected to a voltage source and which are provided with coatings which determine the directions of molecule orientation and which define the molecule alignment direction with mutual angular displacements at their limiting surfaces, therewith causing the liquid crystals to be twisted optically in the absence of voltage between the electrode coatings on the plates, wherein the cells are each mounted between mutually extinguishing polarization filters, and wherein the molecule alignment directions are so turned as to obtain a compensation effect between the respective asymmetrical light absorptions of the cells when a voltage is applied, wherein at least one of the angular displacements of the cells with respect to said molecule alignment directions in the absence of said voltage differs from 90° and is greater than 0° and no greater than 85°.

2. A filter construction according to claim 1, wherein said angular displacement that differ from 90° present an angle of between 20° and 85°.

3. A filter construction according to claim 2, wherein at least the thickness of the crystal which differs from a 90° angular displacement between said alignment directions is so adapted that the product between thickness and the difference between the highest and the lower refractive index for different polarization directions is at most 0.4 $\mu$m, and that each cell has an angular difference between said molecular direction determining coatings of at most 70°.

4. A filter construction according to crystal thickness is at most 3 $\mu$m.

5. A filter construction according to claim 2, comprising one of said liquid crystals having an optimal thickness for said liquid crystal's angular displacement, wherein said optimal thickness is defined by the product of said liquid crystal's optical anisotropy and thickness.

6. A filter construction according to claim 1, wherein the two cells are mutually generally identical; and further comprising a voltage source adapted to apply equal voltages to the cells connected to said electrode-loaded plates.

7. A filter construction according to claim 1, characterized in that the polarization filters between which respective cells are mounted have polarization directions which cross one another at an angle of 90°.

8. A filter construction according to claim 1, wherein at least one of the cells whose molecule-direction determining coatings have a mutual angular displacement below 90° is mounted between polarization filters whose polarization directions coincide with the directions of respective nearest coatings.

9. A filter construction according to claim 1, wherein the bisectrix of the acute angle between the alignment directions that differ from 90° is generally parallel with a bisectrix between the polarization directions of said polarization filters.

10. A filter construction according to claim 1, wherein the bisectrix of the acute angle between the alignment directions that differ from 90° is generally parallel with a polarized direction of one of said polarization filters.

11. A filter construction according to claim 1, wherein the cells have a mutual angular displacement of 90° between the directions of their respective coatings; and in that the respective polarization filters also cross one another at an angle smaller than 90°.

* * * * *